United States Patent
Teague et al.

(10) Patent No.: US 7,322,989 B2
(45) Date of Patent: Jan. 29, 2008

(54) RETRACTABLE GRASPER

(75) Inventors: James A. Teague, Spencer, IN (US); Jeffrey C. Smith, Cloverdale, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 648 days.

(21) Appl. No.: 10/422,499

(22) Filed: Apr. 24, 2003

(65) Prior Publication Data

US 2004/0215212 A1    Oct. 28, 2004

(51) Int. Cl.
*A61B 17/26* (2006.01)

(52) U.S. Cl. .................................... 606/114

(58) Field of Classification Search ............ 606/110, 606/113, 114, 127, 200
See application file for complete search history.

(56) References Cited

U.S. PATENT DOCUMENTS

| | | | | |
|---|---|---|---|---|
| 5,108,406 A | * | 4/1992 | Lee | 606/106 |
| 5,792,145 A | | 8/1998 | Bates et al. | 606/127 |
| 5,944,728 A | | 8/1999 | Bates | 606/127 |
| 5,957,932 A | | 9/1999 | Bates et al. | 606/127 |
| 5,989,266 A | * | 11/1999 | Foster | 606/127 |
| 6,090,129 A | * | 7/2000 | Ouchi | 606/206 |
| 6,096,053 A | | 8/2000 | Bates | 606/159 |
| 6,099,534 A | | 8/2000 | Bates et al. | 606/127 |
| 6,159,220 A | | 12/2000 | Gobron et al. | 606/127 |
| 6,174,318 B1 | | 1/2001 | Bates et al. | 606/127 |
| 6,183,482 B1 | | 2/2001 | Bates et al. | 606/127 |
| 6,187,017 B1 | | 2/2001 | Gregory, Jr. | 606/127 |
| 6,190,394 B1 | | 2/2001 | Lind et al. | 606/127 |
| 6,203,552 B1 | | 3/2001 | Bagley et al. | 606/127 |
| 6,224,612 B1 | | 5/2001 | Bates et al. | 606/114 |
| 6,280,451 B1 | | 8/2001 | Bates et al. | 606/127 |
| 6,319,262 B1 | | 11/2001 | Bates et al. | 606/127 |
| 6,348,056 B1 | | 2/2002 | Bates et al. | 606/114 |
| 6,350,266 B1 | * | 2/2002 | White et al. | 606/114 |
| 6,368,328 B1 | * | 4/2002 | Chu et al. | 606/114 |
| 6,383,196 B1 | | 5/2002 | Leslie et al. | 606/114 |
| 6,443,944 B1 | | 9/2002 | Doshi et al. | 606/1 |
| 6,443,959 B1 | | 9/2002 | Beland et al. | 606/127 |
| 6,491,698 B1 | | 12/2002 | Bates et al. | 606/127 |
| 2001/0047169 A1 | | 11/2001 | McGuckin, Jr. et al. | |

OTHER PUBLICATIONS

International Search Report for International Application No. PCT/US2004/010958 (claiming priority to U.S. Appl. No. 10/422,499) dated Sep. 27, 2004.

* cited by examiner

*Primary Examiner*—Michael J. Hayes
*Assistant Examiner*—Victor Nguyen
(74) *Attorney, Agent, or Firm*—Finnegan, Henderson, Farabow, Garrett and Dunner, L.L.P.

(57) ABSTRACT

A surgical retrieval device, and related method, for removing material, such as calculi, from a patient's body has the ability to capture and release the material. The surgical retrieval device has a handle, a sheath, and a retrieval assembly that includes a plurality of legs. At least one of the legs of the retrieval assembly has a hollow passageway. In one embodiment according to the invention, a prong is disposed within the hollow passageway of the leg.

49 Claims, 15 Drawing Sheets

RETRACTABLE GRASPER

TECHNICAL FIELD

The invention generally relates to retrieval devices for removing biological and/or foreign material from the body of a patient.

BACKGROUND INFORMATION

A surgical retrieval device can be used to retrieve calculi from a body. The device can be used through an endoscope or a laparoscope, or it may be used without the aid of an endoscope or a laparoscope.

One type of known surgical retrieval device has a sheath and a basket moveable in and out of the sheath. The basket can be collapsed within the sheath to achieve a reduced diameter profile. The basket can be expanded when it extends beyond the distal end of the sheath.

Forceps also can be used to retrieve material from a body.

SUMMARY OF THE INVENTION

The invention generally relates to devices and methods for the retrieval of material from the body of a patient. The devices and methods allow for the easy capture of material and also avoid damaging the lining of the body tract in which the material resides, particularly in those clinical situations where the material must be released and the device must be withdrawn from the body. One embodiment of a device according to the invention is a substantially atraumatic surgical retrieval device which is capable of capturing and releasing biological and/or foreign material (e.g., calculi).

In one aspect of the invention, a surgical retrieval device includes a handle, at least one sheath having a proximal end joined to the handle, a distal end, and a lumen, and a retrieval assembly comprising a plurality of legs. At least one of the legs of the retrieval assembly comprises a hollow passageway for receiving a prong. The retrieval assembly achieves a collapsed position when within the lumen of the sheath and an expanded position when beyond the distal end of the sheath. In a particular embodiment according to this aspect of the invention, each of the plurality of legs of the retrieval assembly comprises a proximal end fixed to a base of the retrieval assembly and a distal end unfixed to the distal end of any of the other legs.

Various other embodiments of this aspect of the invention include the following features. A first actuating mechanism may be positioned on the handle. The first actuating mechanism may be operatively coupled to the sheath for reciprocal movement of the sheath to achieve the collapsed position and the expanded position of the retrieval assembly. Alternatively, the first actuating mechanism may be operatively coupled to the retrieval assembly for reciprocal movement of the retrieval assembly to achieve the collapsed position of the retrieval assembly within the lumen of the sheath and the expanded position of the retrieval assembly beyond the distal end of the sheath. In one embodiment, the first actuating mechanism may be, for example, a thumb slide, or, alternatively, a turn knob or a lever arm.

In some embodiments, the retrieval assembly further includes a prong. The prong may be slideably disposed within the hollow passageway of the leg of the retrieval assembly and may include a modified gripping surface. The prong can be moved between a sheathed position, wherein the prong is enclosed within the hollow passageway of the leg of the retrieval assembly, and a deployed position, wherein the prong is extended beyond the distal end of the leg of the retrieval assembly. When the prong achieves the deployed position, it may be oriented differently with respect to the sheath, as compared to the leg's orientation with respect to the sheath.

In another embodiment according to the invention, a second actuating mechanism may be positioned on the handle. The second actuating mechanism may be operatively coupled to the prong and may be used to extend the prong to a deployed position beyond the distal end of the leg or to retract the prong to a sheathed position within the hollow passageway of the leg. Alternatively, the second actuating mechanism may be operatively coupled to one of the legs and may be used to advance the leg or to withdraw the leg over the prong. In yet another embodiment, the surgical retrieval device includes both a first actuating mechanism for actuating the legs and a second actuating mechanism for actuating the prong. The first and second actuating mechanisms are positioned on the handle.

In still another embodiment of the invention, a cross-section of the prong may be of the same shape as a cross-section of the hollow passageway of the leg. For example, the cross-section of both the prong and the hollow passageway may be round, rectangular, D-shaped, or V-shaped.

In another aspect, the invention provides a retrieval assembly for a surgical retrieval device. The retrieval assembly includes a plurality of legs, at least one of which further includes a hollow passageway, and a prong. The prong is disposed within the hollow passageway of the leg.

In another aspect, the invention provides a method of retrieving a material from a body. The method includes the steps of inserting a surgical retrieval device according to the invention into the body, positioning the retrieval assembly, in the expanded position, near the material to be removed, capturing the material with the retrieval assembly, and withdrawing the retrieval device from the body to remove the captured material from the body. In an embodiment of this aspect of the invention, the captured material includes a calculus, such as a urinary bladder stone.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1A:
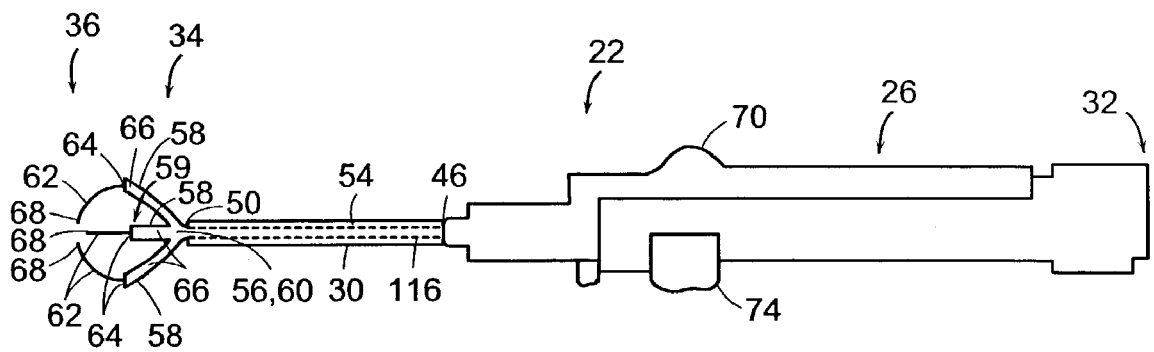
FIG. 1A illustrates a plan view of one embodiment of a surgical retrieval device according to the invention.

Referring to FIG. 1A, a surgical retrieval device 22 according to the invention has a handle 26, an outer sheath 30, and a retrieval assembly 34. The handle 26 is located at the proximal end 32 of the surgical retrieval device 22, i.e., at the end of the surgical retrieval device 22 that is closest to the operator. The retrieval assembly 34 is located at the opposite, distal end 36 of the surgical retrieval device 22. In one embodiment according to the invention, the handle 26 includes a first actuating mechanism 70 and a second actuating mechanism 74. Alternatively, in other embodiments according to the invention, the handle 26 may include, for example, only one actuating mechanism, three actuating mechanisms, or any number of actuating mechanisms. The outer sheath 30 has a proximal end 46 and a distal end 50. A longitudinally disposed lumen 54 extends from the proximal end 46 of the outer sheath 30 to the distal end 50 of the outer sheath 30. A first elongate member 116 axially extends in the lumen 54 of the outer sheath 30 from the handle 26 to the base 56 of the retrieval assembly 34, where it is joined to the retrieval assembly 34.

Figure 1B:
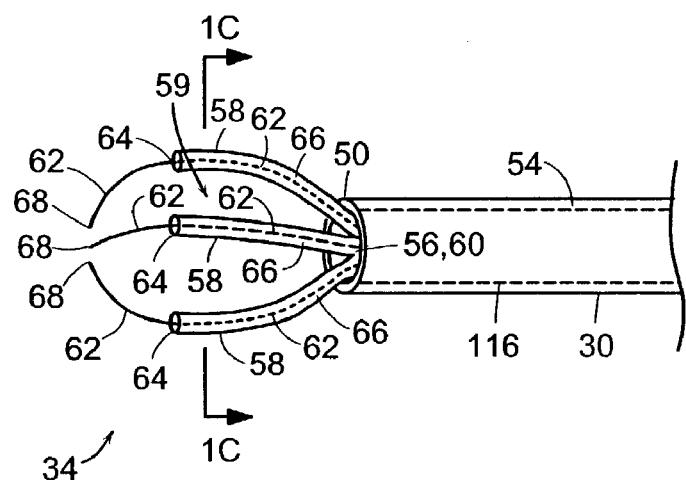
FIG. 1B illustrates an enlarged view of one embodiment of the distal end of the surgical retrieval device illustrated in FIG. 1A.
Figure 1C:
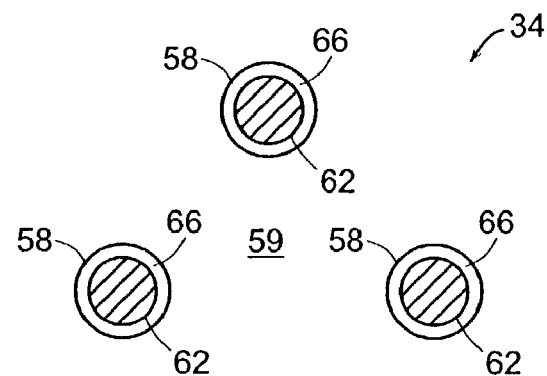
FIG. 1C illustrates a cross-sectional view taken along a line 1C-1C of FIG. 1B.

In general, referring now to FIGS. 1B and 1C, the retrieval assembly 34 is formed by a plurality of legs 58, for example, three legs 58. The legs 58 may be made from a variety of materials such as metal, for example, nickel-titanium or stainless steel. Alternatively, the legs 58 may be made from plastic or a combination of metal and plastic. As shown, the legs 58 have a fixed proximal end 60, where each of the legs 58 are fixed to the retrieval assembly base 56, and an unattached distal end 64, where the distal end 64 of the legs is free and not connected to the distal end 64 of any of the other legs 58. In one embodiment according to the invention, at least one of the legs 58 is straight. Alternatively, at least one of the legs 58 is curved. At least one of the legs 58, and preferably all of the legs 58, have a hollow passageway 66 that extends from the proximal end 60 of the leg 58 to the distal end 64 of the leg 58. Alternatively, the hollow passageway 66 extends along only a portion of the length of the leg 58.

A prong 62 may be positioned in, and may be slideably moveable in, the hollow passageway 66 of each of one or more legs 58 of the retrieval assembly 34. The prongs 62 are typically straight or gently curved wires. The distal end 68 of the prong 62 may extend from the free distal end 64 of the leg 58 of the retrieval assembly 34 in which the prong 62 is enclosed. In one embodiment, the distal end 68 of the prong 62 is curved with the tip of the prong 62 pointing toward the center of a lumen 59 of the retrieval assembly 34. In an alternative embodiment (not shown), the legs 58 of the retrieval assembly 34 are curved inwardly and the prongs 62 which extend from the distal end 64 of the legs 58 are straight.

In one embodiment according to the invention, the outer sheath 30 of the surgical retrieval device 22 is operatively joined to the first actuating mechanism 70 or the second actuating mechanism 74 on the handle 26 of the surgical retrieval device 22. In another embodiment, the prongs 62 are operatively joined to the first actuating mechanism 70 or the second actuating mechanism 74 on the handle 26 of the surgical retrieval device 22. In yet another embodiment, the first elongate member 116 is operatively joined to the first actuating mechanism 70 or the second actuating mechanism 74 on the handle 26 of the surgical retrieval device 22.

Figure 2:
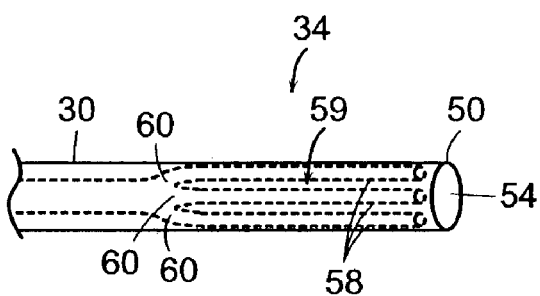
FIG. 2 illustrates an enlarged view of one embodiment of one position of the retrieval assembly at the distal end of the surgical retrieval device illustrated in FIG. 1A.

The retrieval assembly 34 according to the invention can achieve a collapsed position and an expanded position. Referring now to FIG. 2, in one embodiment, the retrieval assembly 34 is enclosed, in a collapsed position, within the lumen 54 of the outer sheath 30. The retrieval assembly 34 may be reciprocally moved between the collapsed position shown in FIG. 2 to an expanded position shown in FIGS. 3 and 4. In the expanded position shown in FIGS. 3 and 4, the legs 58 of the retrieval assembly 34 are extended beyond the distal end 50 of the outer sheath 30.

Figure 3:
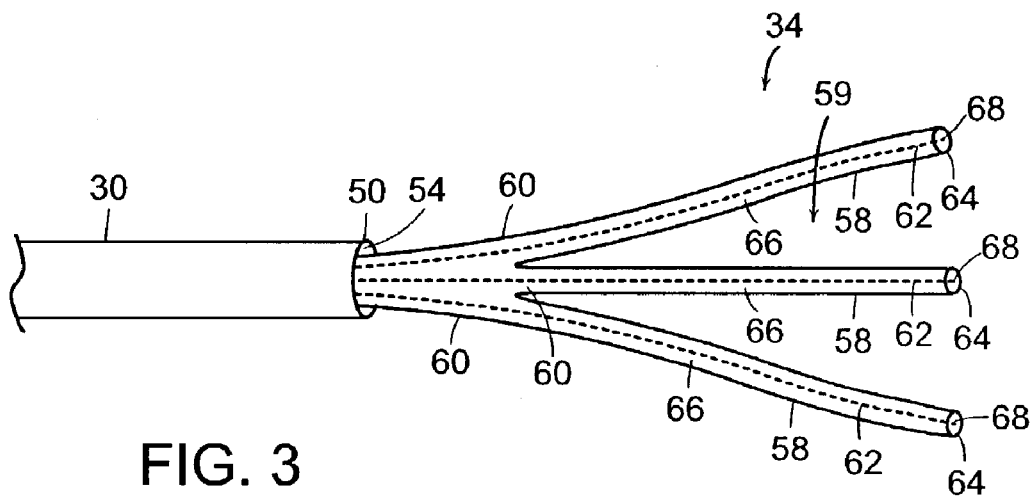
FIG. 3 illustrates an enlarged view of another embodiment of one position of the retrieval assembly at the distal end of the surgical retrieval device illustrated in FIG. 1A.
Figure 4:
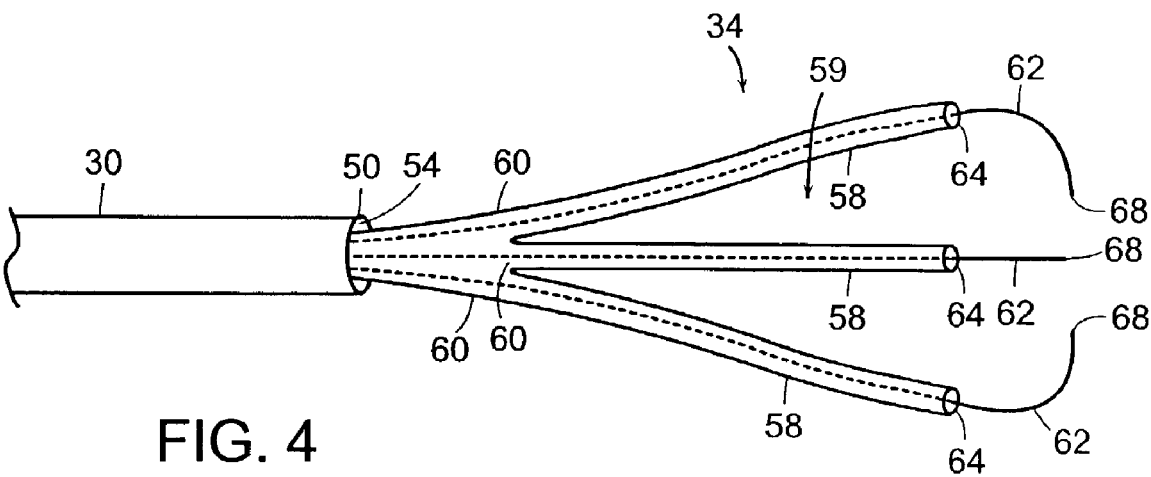
FIG. 4 illustrates an enlarged view of another embodiment of one position of the retrieval assembly at the distal end of the surgical retrieval device illustrated in FIG. 1A.

In one embodiment according to the invention, the retrieval assembly 34 alternates between the collapsed position illustrated in FIG. 2 and the expanded position illustrated in FIGS. 3 and 4 by slideable movement of the first elongate member 116 in the lumen 54 of the outer sheath 30. Alternatively, the retrieval assembly 34 can move between the collapsed and expanded positions by advancing the outer sheath 30 over the stationary retrieval assembly 34 and the first elongate member 116 to collapse the retrieval assembly 34 within the outer sheath 30 and by withdrawing the moveable outer sheath 30 to expose the stationary retrieval assembly 34, allowing it to open and expand.

In general, both types of retrieval assembly/outer sheath movement configurations and related handle mechanisms are known, and can be seen in existing product designs available from, for example, Boston Scientific Corporation (Natick, Mass.). With the retrieval assembly 34 collapsed within the outer sheath 30 as illustrated in FIG. 2, the outer sheath 30 can be inserted into the body of a patient by an operator to an anatomical site where the material to be retrieved is located (e.g., a stone in the ureter). By placing the retrieval assembly 34 in its open/expanded position illustrated in FIG. 3, the retrieval assembly dilates the body tract and can be positioned by the operator adjacent the material to be retrieved.

Referring to FIG. 3, the prongs 62 are enclosed within the hollow passageway 66 of the legs 58 in a sheathed position. The prongs 62 may be moved from the sheathed position to a deployed position, such that the prongs 62 are moved distally (i.e., away from the operator) beyond the free distal ends 64 of the legs 58, as illustrated in FIG. 4.

Figure 5:
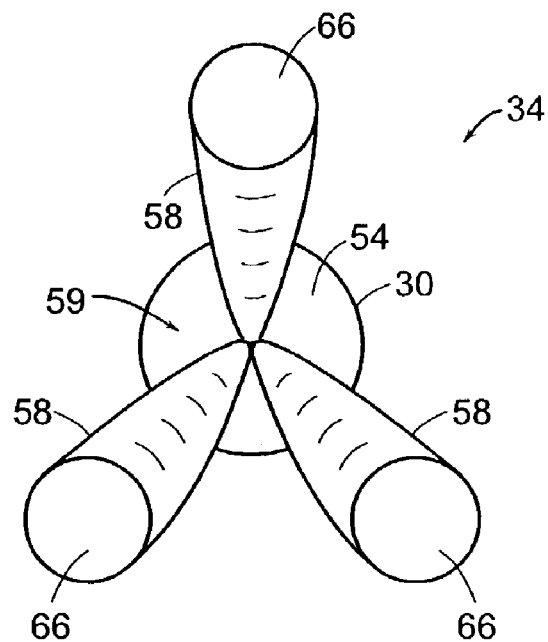
FIG. 5 illustrates an end view of the retrieval assembly illustrated in FIG. 3 showing the legs of the retrieval assembly extended from the distal end of the outer sheath.

Referring now to FIGS. 3 and 5, relative sliding movement between the outer sheath 30 and the legs 58 of the retrieval assembly 34 extends the legs 58 beyond the distal end 50 of the outer sheath 30. When the legs 58 exit the lumen 54 at the distal end 50 of the outer sheath 30, the legs 58 project outwards and diverge from one another, such that the retrieval assembly 34 achieves the expanded position illustrated in FIGS. 3 and 5.

Figure 6:
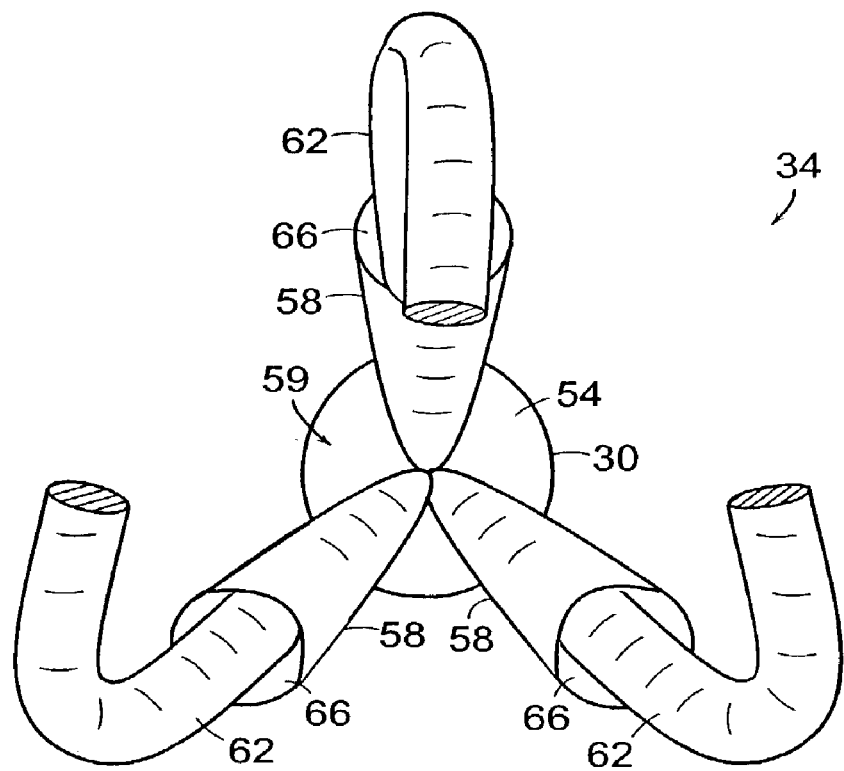
FIG. 6 illustrates an end view of the retrieval assembly illustrated in FIG. 4 showing the prongs of the retrieval assembly fully deployed from the extended legs of the retrieval assembly.

Referring now to FIGS. 4 and 6, relative sliding movement between the legs 58 and the prongs 62 extends the prongs 62 beyond the distal ends 64 of the legs 58. In one embodiment according to the invention, for example, as illustrated in FIG. 4, the distal ends 68 of the prongs 62 may be curved inward toward the center of the lumen 59 of the retrieval assembly 34. As such, when the distal ends 68 of the prongs 62 exit from the hollow passageway 66 at the distal end 64 of each of the legs 58 to achieve the deployed position, the distal ends 68 of the prongs 62 converge towards one another, such that the prongs 62 and the legs 58 are oriented differently with respect to the sheath 30.

Figure 7A:
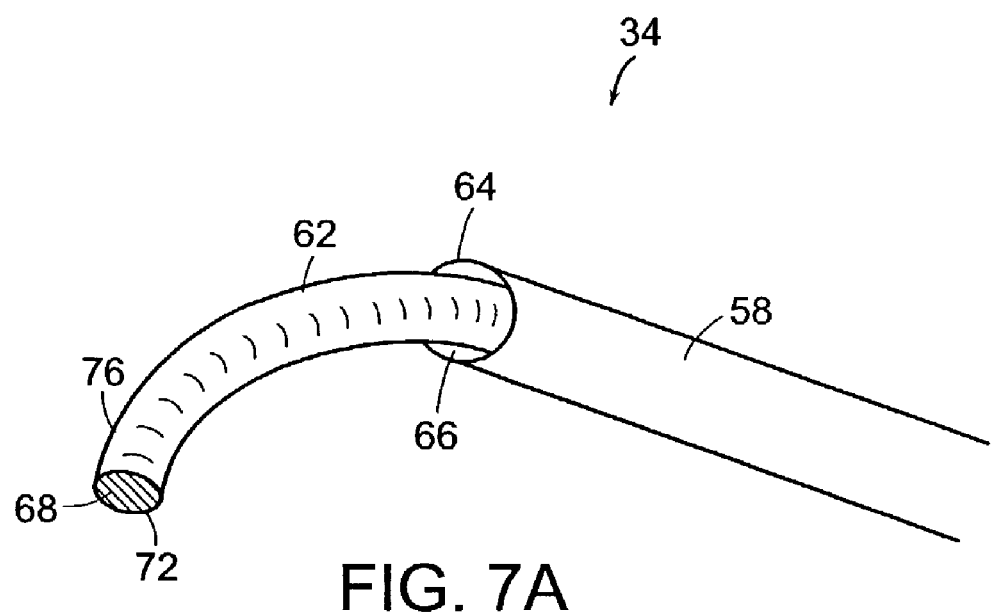
FIG. 7A illustrates a perspective view of one embodiment of a prong deployed from a leg of the retrieval assembly according to the invention.
Figure 7B:
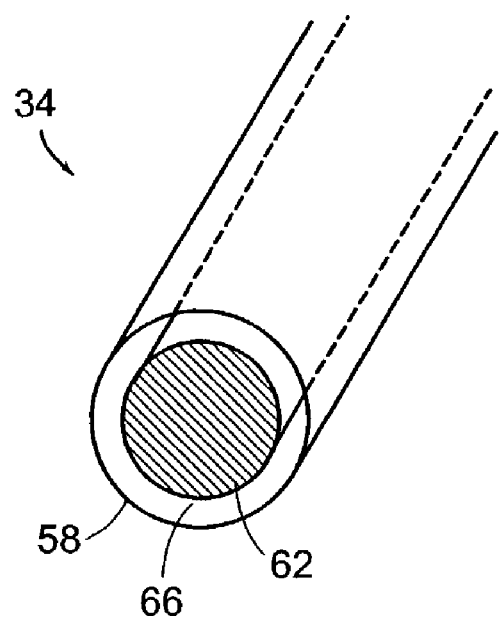
FIG. 7B illustrates the prong retracted into the leg illustrated in FIG. 7A.
Figure 7C:
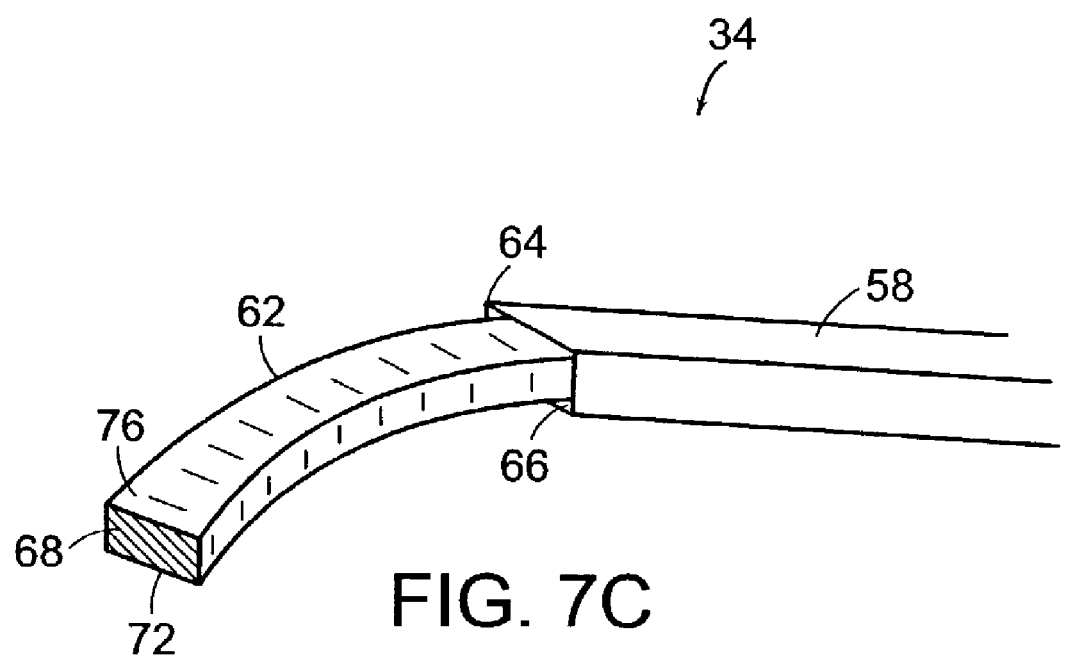
FIG. 7C illustrates a perspective view of another embodiment of a prong deployed from a leg of the retrieval assembly according to the invention.
Figure 7D:
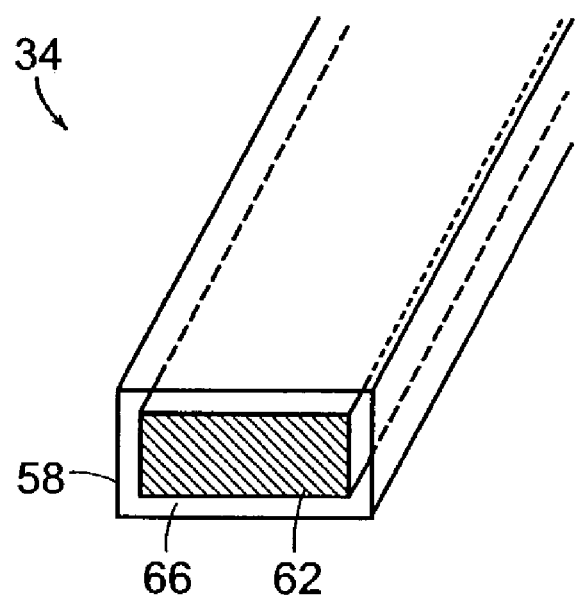
FIG. 7D illustrates the prong retracted into the leg illustrated in FIG. 7C.
Figure 7E:
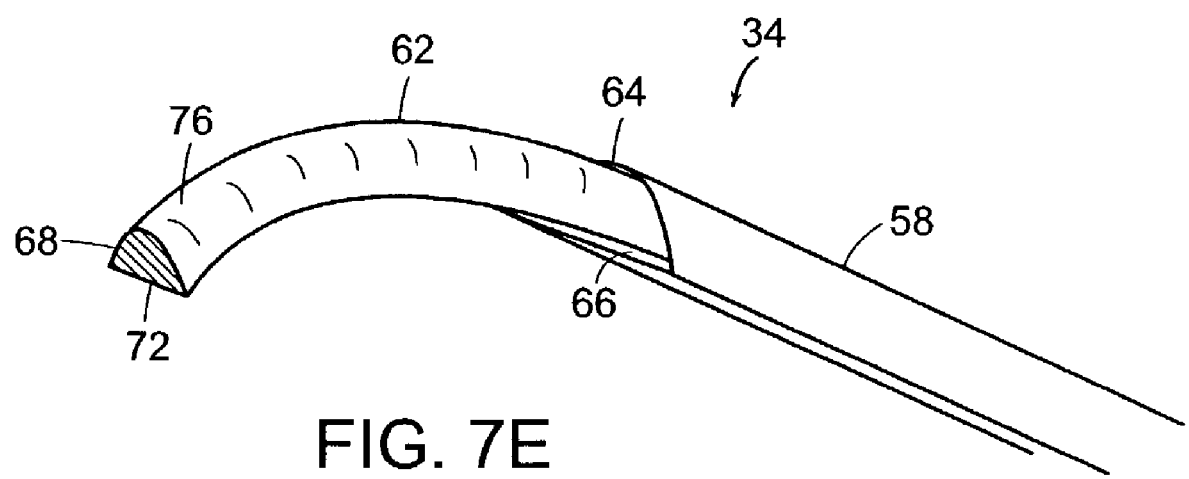
FIG. 7E illustrates a perspective view of another embodiment of a prong deployed from a leg of the retrieval assembly according to the invention.
Figure 7F:
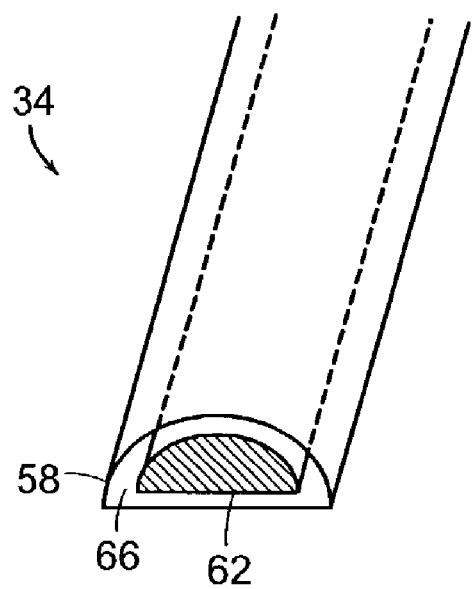
FIG. 7F illustrates the prong retracted into the leg illustrated in FIG. 7E.
Figure 7G:
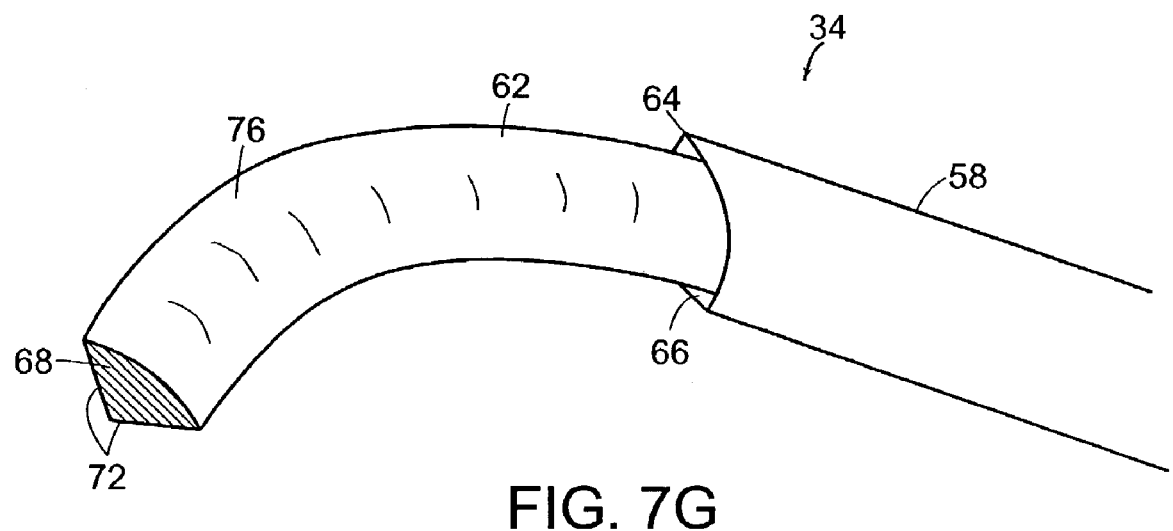
FIG. 7G illustrates a perspective view of another embodiment of a prong deployed from a leg of the retrieval assembly according to the invention.
Figure 7H:
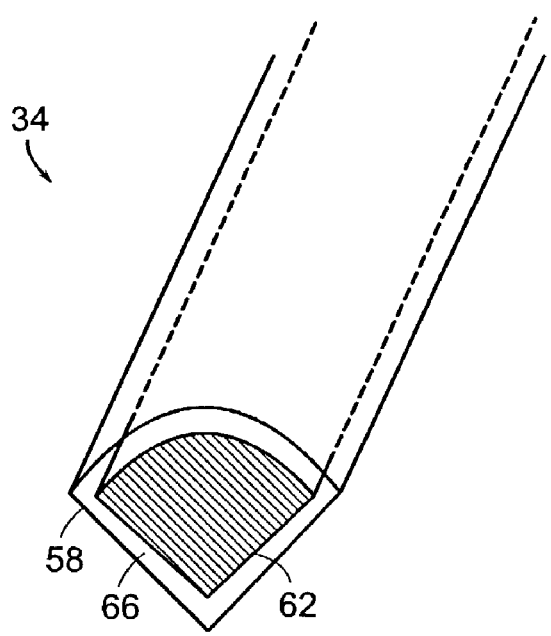
FIG. 7H illustrates the prong retracted into the leg illustrated in FIG. 7G.

Referring now to FIGS. 7A-7H, in one embodiment according to the invention, the prong 62 has the same cross-sectional shape as the hollow passageway 66 in which the prong 62 is sheathed. For example, the cross-sectional shape of the prong 62 and the cross-sectional shape of the hollow passageway 66 may be round, as illustrated in FIGS. 7A and 7B, rectangular, as illustrated in FIGS. 7C and 7D, D-shaped with a rounded outer surface and a flattened inner surface, as illustrated in FIGS. 7E and 7F, or V-shaped with a rounded outer surface and a wedge-shaped inner surface, as illustrated in FIGS. 7G and 7H. By constructing the prong 62 and the hollow passageway 66 of the leg 58 in which the prong 62 is sheathed to have the same cross-sectional shape, the clearance between the outside surface of the prong 62 and the inner surface of the leg 58 in which the prong 62 is sheathed is minimized, thereby preventing the prong 62 from twisting or bending in the hollow passageway 66 when the prong 62 is retracted into the leg 58.

Figure 7I:
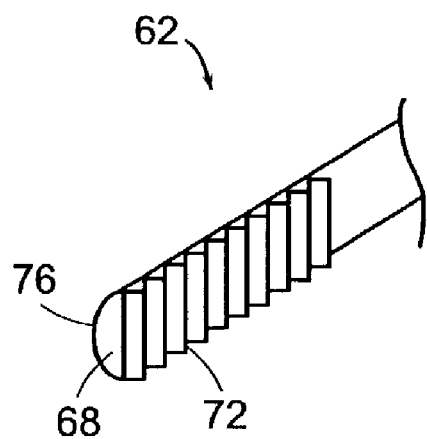
FIG. 7I illustrates a perspective view of one embodiment of a prong of the retrieval assembly according to the invention.

Referring now to FIG. 7I, in one embodiment according to the invention, the inner surface 72 of the prong 62 is modified to be rougher than the outer surface 76 of the prong 62. The modified roughened inner surface 72 enhances the gripping and retention ability of the retrieval assembly 34. The inner surface 72 may be rough along the entire length of the prong 62. In another embodiment, the inner surface 72 is rough for only a portion of the length of prong 62. The roughness on the inner surface 72 of the prong 62 can be achieved, for example, by serrations, teeth, or by pitting, for example, by etching, sand blasting, or a variety of other known techniques. The prong 62 may be made from a metal, such as, for example, a high tensile type of metal, including, but not limited to, stainless steel, titanium, nickel-titanium, nickel-chromium, or cobalt chromium.

Figure 7J:
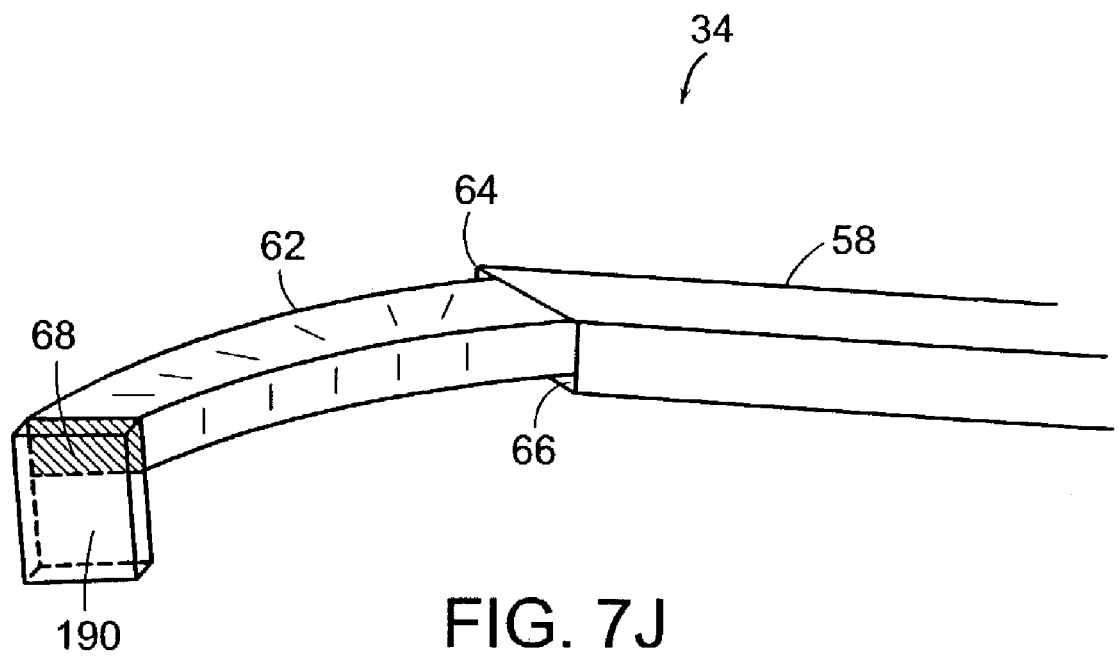
FIG. 7J illustrates a perspective view of one embodiment of a hook positioned at the distal end of one embodiment of a prong of the retrieval assembly according to the invention.

Referring now to FIG. 7J, in one embodiment according to the invention, a hook 190 may be positioned at the distal end 68 of the prong 62 to further enhance the grasping and retention ability of the retrieval assembly 34. The hook 190 may be inclined, preferably at 90 degrees, relative to the distal end 68 of the prong 62.

Figure 8A:
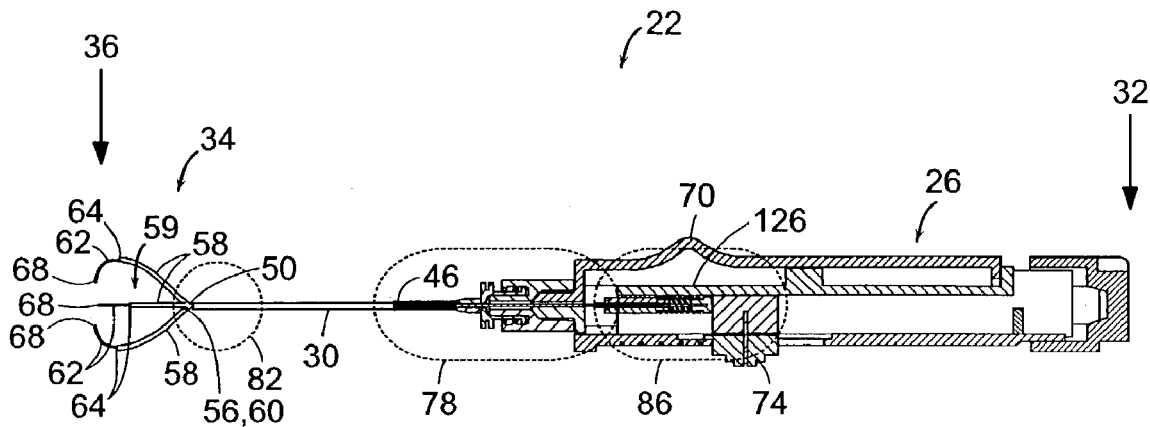
FIG. 8A is a detailed plan view of the surgical retrieval device illustrated in FIG. 1A.
Figure 8B:
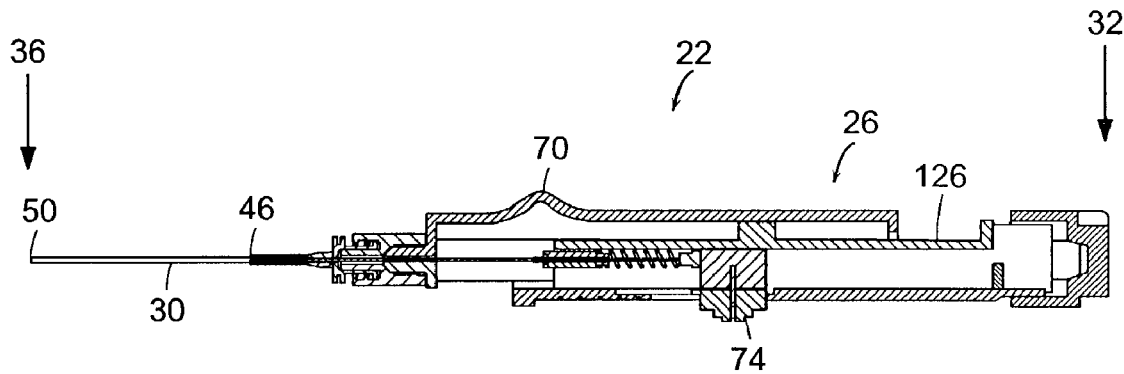
FIG. 8B is a detailed plan view of the surgical retrieval device illustrated in FIG. 8A with the retrieval assembly withdrawn into the sheath.
Figure 8C:
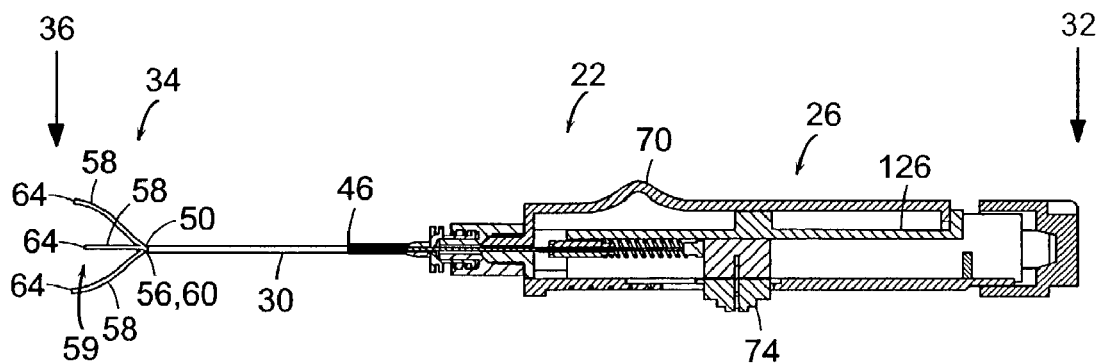
FIG. 8C is a detailed plan view of the surgical retrieval device illustrated in FIG. 8A with the prongs withdrawn into the legs of the retrieval assembly.

Referring now to FIG. 8A, in one embodiment of the handle 26 of the surgical retrieval device 22 according to the invention, a first thumb slide 70 is positioned on the handle 26 and is actuateably coupled to the outer sheath 30. A second thumb slide 74 is positioned on the handle 26 is and actuateably coupled to the prongs 62. Referring now to FIG. 8B, when the first thumb slide 70 is advanced to its furthest distal position on the handle 26, the retrieval assembly 34 is enclosed in the collapsed position within the lumen 54 of the outer sheath 30. Referring now to FIG. 8C, when the first thumb slide 70 is withdrawn proximally, the outer sheath 30 is withdrawn proximally to expose the legs 58 of the retrieval assembly 34 beyond the distal end 50 of the outer sheath 30. The retrieval assembly 34 thereby achieves the expanded position beyond the distal end 50 of the outer sheath 30 when the first thumb slide 70 is withdrawn proximally. Referring again to FIG. 8A, when the second thumb slide 74 is advanced distally, the prongs 62 are advanced distally and extend from the hollow passageway 66 at the distal ends 64 of the legs 58 to achieve the deployed position of the prongs 62. Referring again to FIG. 8C, when the second thumb slide 74 is withdrawn proximally, the prongs 62 are withdrawn into the hollow passageway 66 of the legs 58 to achieve the sheathed position of the prongs 62. Referring again to FIG. 8B, when the first thumb slide 70 is advanced distally, the outer sheath 30 advances distally, enclosing the legs 58 of the retrieval assembly 34. The retrieval assembly 34 therefore achieves the collapsed position within the lumen 54 of the outer sheath 30.

Figure 9A:
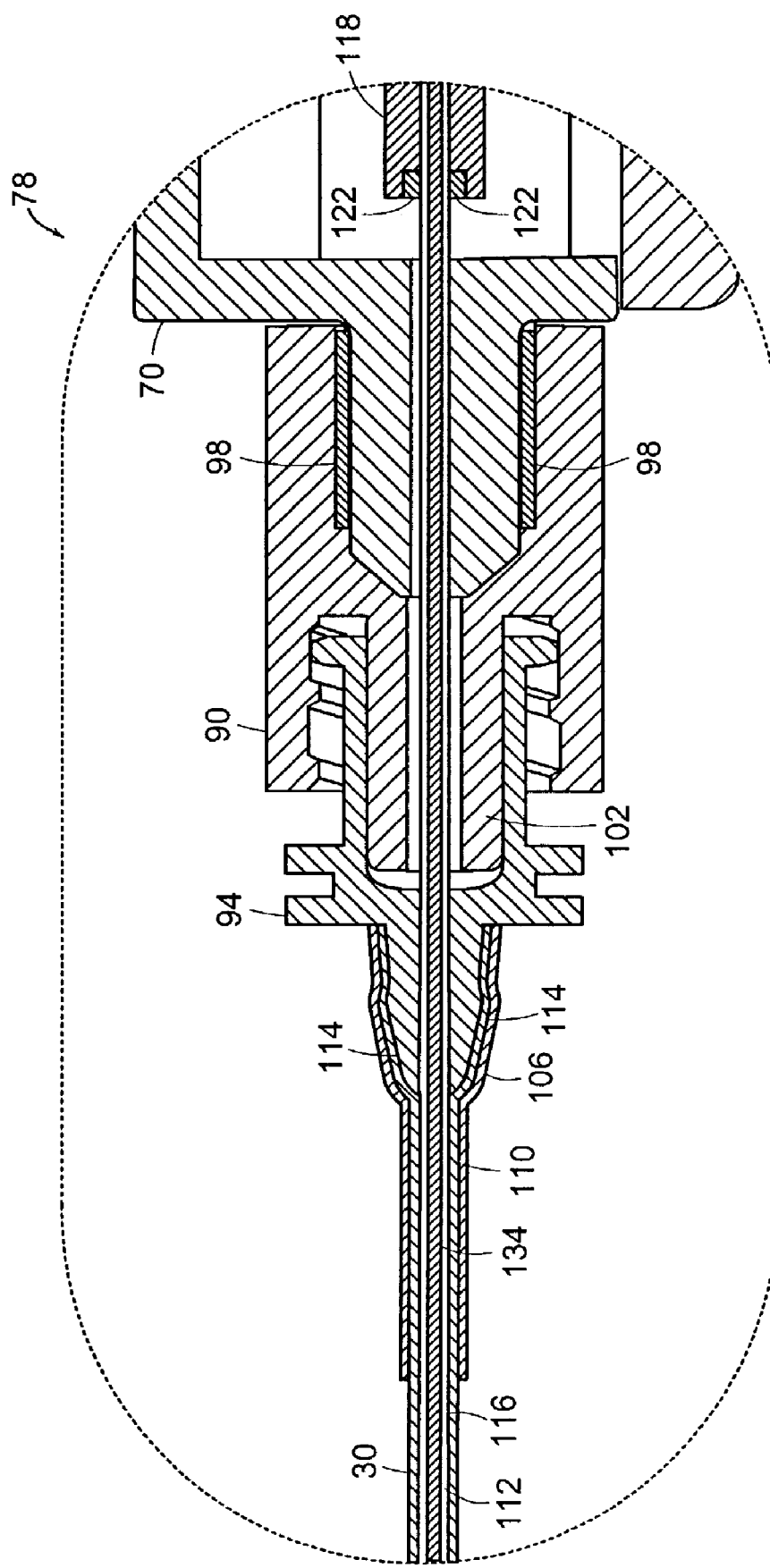
FIGS. 9A, 9B, and 9C are enlarged views of delimited region 78, delimited region 82, and delimited region 86 illustrated in FIG. 8A, respectively.
Figure 9B:
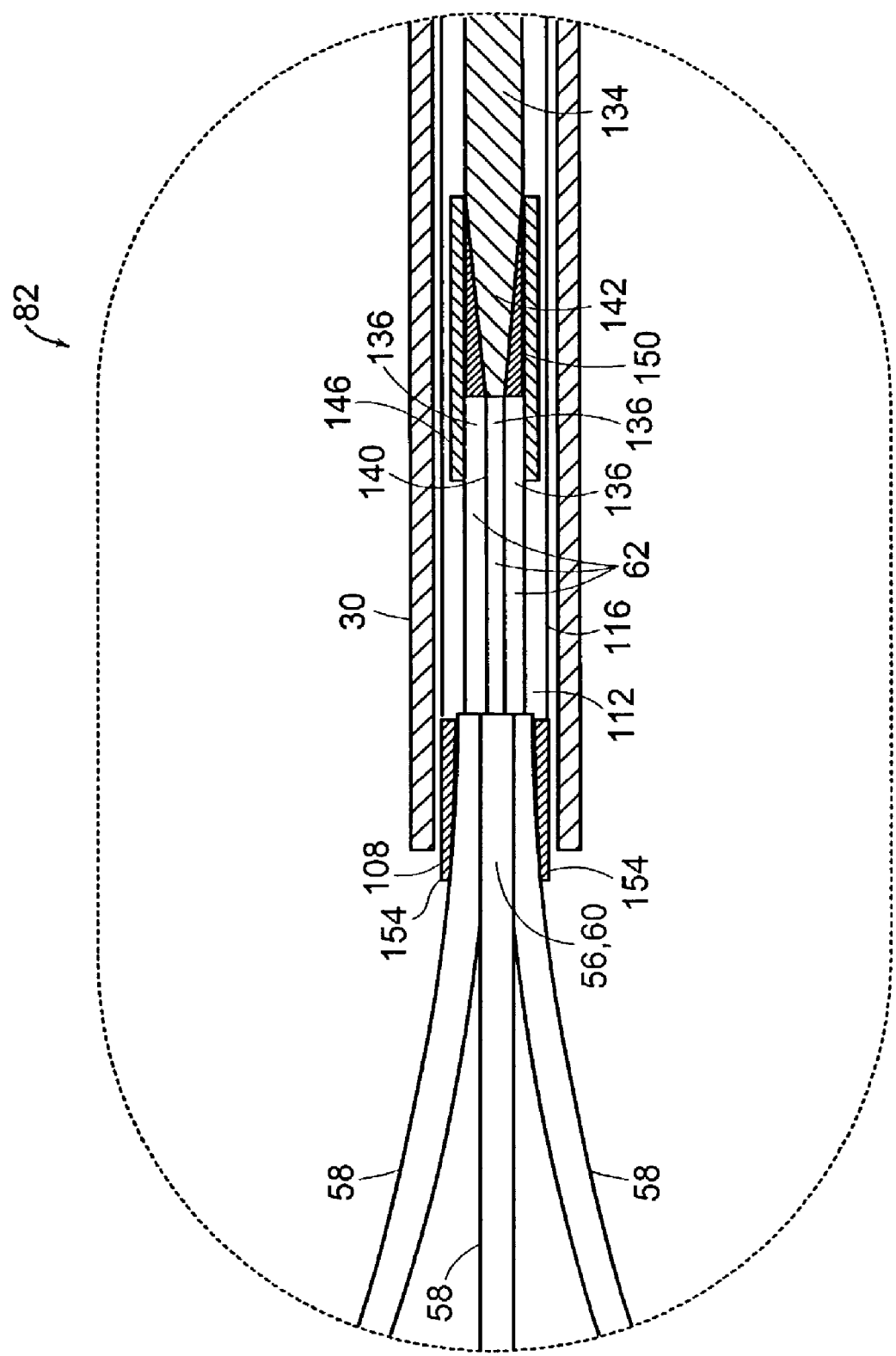
Figure 9C:
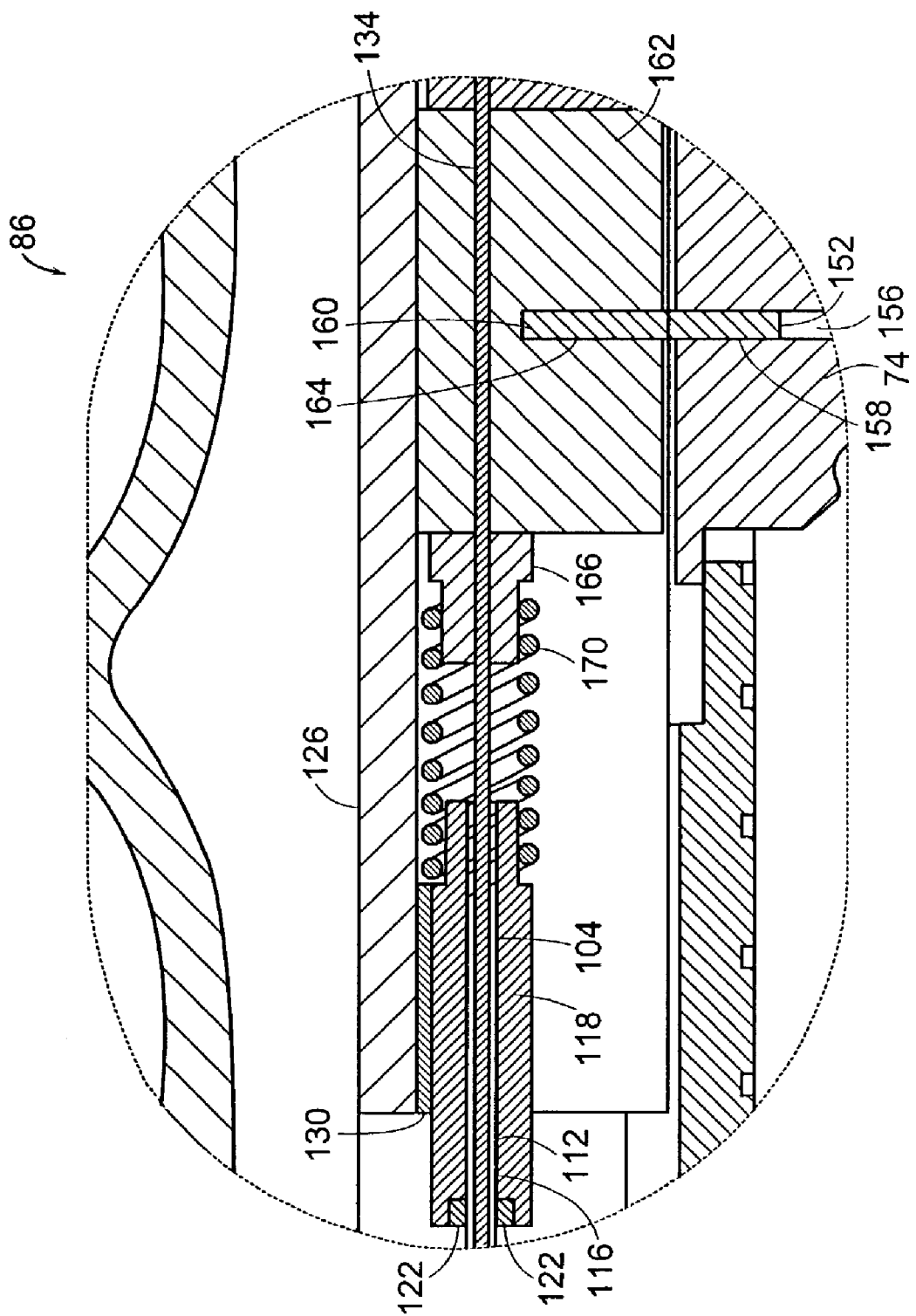

To better understand this embodiment of the actuation and operation of the retrieval assembly 34, enlarged views of the delimited regions 78, 82, and 86 in FIG. 8A are shown in FIGS. 9A, 9B, and 9C, respectively. Referring to the enlarged view of delimited region 78 in FIG. 9A, in one embodiment according to the invention, the first thumb slide 70 is actuateably coupled to the outer sheath 30 through a cap 90 and a luer member 94. At its proximal end, the cap 90 is affixed to the first thumb slide 70 by, for example, an adhesive 98. At its distal end, the cap 90 has a nose cone 102. The proximal end of the luer member 94 is threaded or screwed on to the nose cone 102. At its distal end, the luer member 94 has a tapered nose 106 and a distal tip 110. The outer sheath 30 is positioned within the distal tip 110 and tapered nose 106 of the luer member 94 and is affixed to the tapered nose 106 by, for example, molten plastic 114. Accordingly, reciprocating longitudinal movement of the first thumb slide 70 reciprocatingly moves the cap 90, the luer member 94, and the outer sheath 30 longitudinally.

In one embodiment according to the invention, the first elongate member 116 is disposed within the lumen 54 of the outer sheath 30. The first elongate member 116 has a proximal end 104 (FIG. 9C), a distal end 108 (FIG. 9B), and a lumen 112 extending from the proximal end 104 to the distal end 108. Referring to FIG. 9C, the first elongate member 116 is fixed in position and held stationary by being permanently attached at its proximal end 104 to a hub assembly 118 by, for example, an adhesive 122. The hub assembly 118 is itself permanently affixed to the handle body 126 of the handle 26 by, for example, an adhesive 130. A second elongate member 134 is disposed within the lumen 112 of the first elongate member 116.

Referring to FIG. 9B, the distal end 142 of the second elongate member 134 is tapered to form a tapered end 142. The tapered end 142 and the proximal end 136 of each of the prongs 62 are positioned within a lumen 140 of a joining cannula 146. The proximal end 136 of each of the prongs 62, the tapered end 142, and the joining cannula 146 are affixed together by, for example, a solder 150, such that longitudinal movement of the second elongate member 134 results in sliding movement of the prongs 62.

With continued reference to FIG. 9B, the proximal ends 60 of the legs 58 are attached to the distal end 108 of the first elongate member 116 by, for example, an adhesive 154. In one embodiment according to the invention, each leg 58 is separate and independent from each other leg 58 and is separately attached at its separate proximal end 60 to the first elongate member 116. Alternatively, the legs 58 can share a common proximal end 60, by being joined directly to one another at their proximal ends 60, and the common proximal end 60 may then be attached to the first elongate member 116.

Referring again to FIG. 9C, in one embodiment according to the invention, the second thumb slide 74 is actuateably coupled to the prongs 62 (shown in FIG. 9B) through a pin 158, a slide block 162, and the second elongate member 134. The pin 158 couples the second thumb slide 74 to the slide block 162. The bottom end 152 of the pin 158 is fitted into a bore 156 extending into the second thumb slide 74 and the top end 160 of the pin 158 is fitted into a bore 164 extending into the slide block 162. Longitudinal movement of the second thumb slide 74 therefore also results in longitudinal movement of the slide block 162. The second elongate member 134 is glued, for example, to the slide block 162 and therefore moves longitudinally in tandem with the slide block 162. Thus, longitudinal movement of the second thumb slide 74 results in longitudinal movement of the second elongate member 134 and, consequently, in sliding movement of the prong 62 in the hollow passageway 66 of each of the legs 58 of the retrieval assembly 34, as described above.

With continued reference to FIG. 9C, coupled to the slide block 162 is a push block 166. When the slide block 162 is advanced distally by advancing the second thumb slide 74 distally, the push block 166 is also advanced distally and compresses a return spring 170 against the hub assembly 118. When the second thumb slide 74 is released, the return spring 170 expands proximally to regain its original form and the push block 166, the slide block 162 and the second thumb slide 74 are returned proximally to their original withdrawn positions. Consequently, the second elongate member 134 is withdrawn proximally and the prongs 62 are therefore retracted proximally to achieve the sheathed position within the legs 58 of the retrieval assembly 34.

In another embodiment according to the invention, the first thumb slide 70 may be actuateably coupled to the proximal end 104 of the first elongate member 116 and the distal end 108 of the first elongate member 116 may be actuateably coupled to the legs 58 of the retrieval assembly 34. The second thumb slide 74 is actuateably coupled to the second elongate member 134 which is actuateably coupled to the prongs 62. The outer sheath 30 is fixed in position and remains stationary. Longitudinal movement of the first thumb slide 70 results in sliding movement of the legs 58 relative to the outer sheath 30. The legs 58 are deployed beyond the distal end 50 of the outer sheath 30, when the first thumb slide 70 is advanced distally. The legs 58 are retracted into the distal end 50 of the outer sheath 30, when the first thumb slide 70 is withdrawn proximally.

In yet another embodiment, the first thumb slide 70 is actuateably coupled to the outer sheath 30, and the second thumb slide 74 may be actuateably coupled to the proximal end 104 of the first elongate member 116 and the distal end 108 of the first elongate member 116 may be actuateably coupled to the legs 58 of the retrieval assembly 34. The prongs 62 are fixed in position and remain stationary. Longitudinal movement of the second thumb slide 74 results in sliding movement of the legs 58 relative to the prongs 62. When the second thumb slide 74 is withdrawn proximally, the legs 58 are retracted proximally such that the prongs 62 achieve the deployed position. When the second thumb slide 74 is advanced distally, the legs 58 are advanced distally such that the prongs 62 achieve the sheathed position.

Figure 10A:
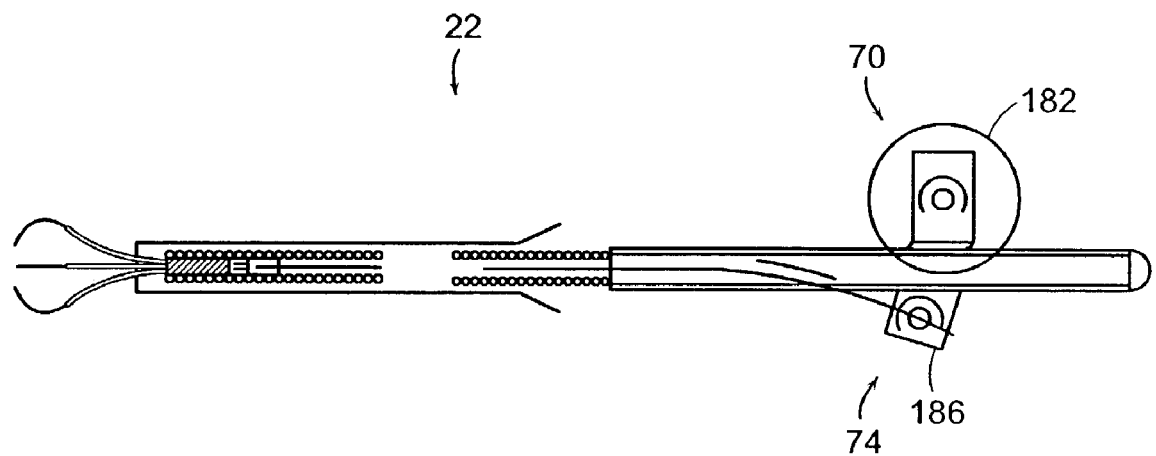
FIGS. 10A-10B are plan views showing select components of alternative embodiments of the surgical retrieval device in accordance with the invention.
Figure 10B:
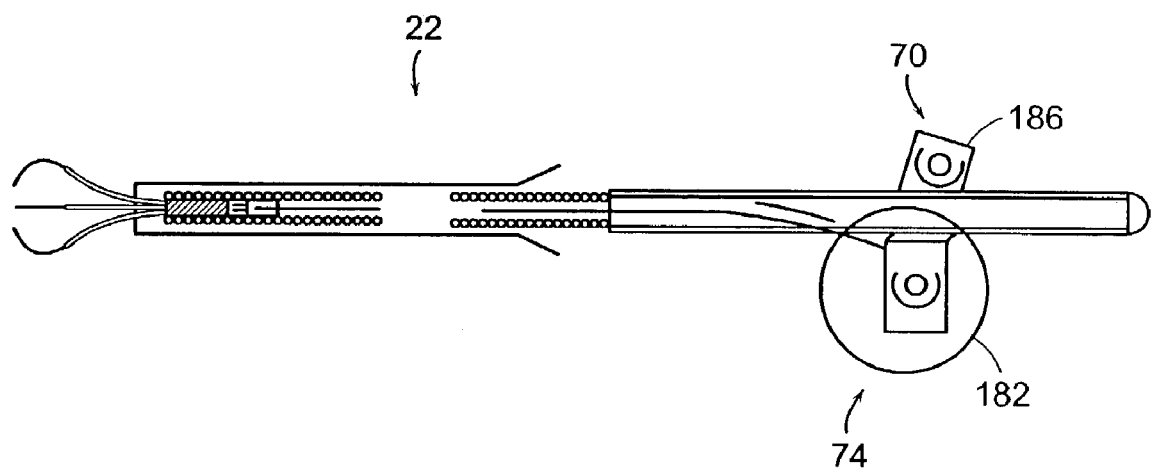

In another embodiment, the first actuating mechanism 70 or the second actuating mechanism 74 can be a turn knob 182, as shown in FIGS. 10A and 10B, respectively. Alternatively, the first actuating mechanism 70 or the second actuating mechanism 74 can be a lever arm 186, as shown in FIGS. 10B and 10A, respectively.

Figure 11A:
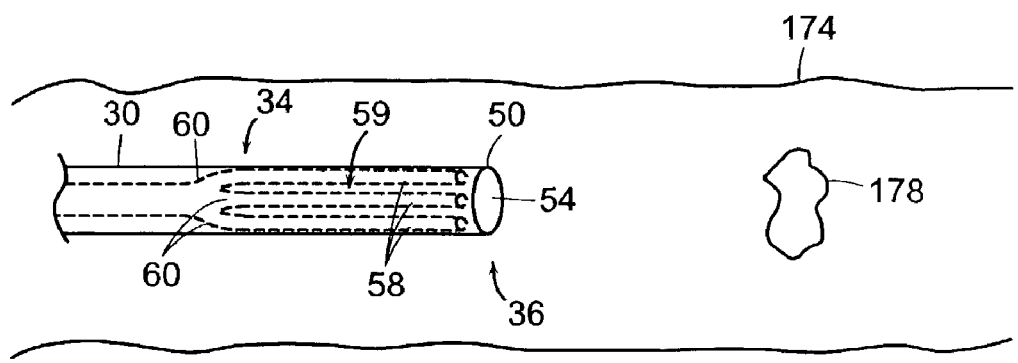
FIGS. 11A-11E illustrate the steps in one embodiment of a clinical application of the surgical retrieval device according to the invention.
Figure 11B:
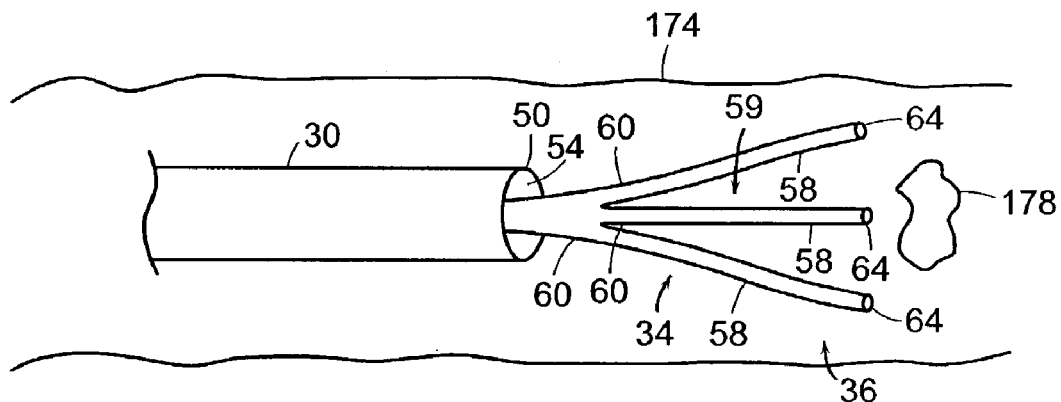
Figure 11C:
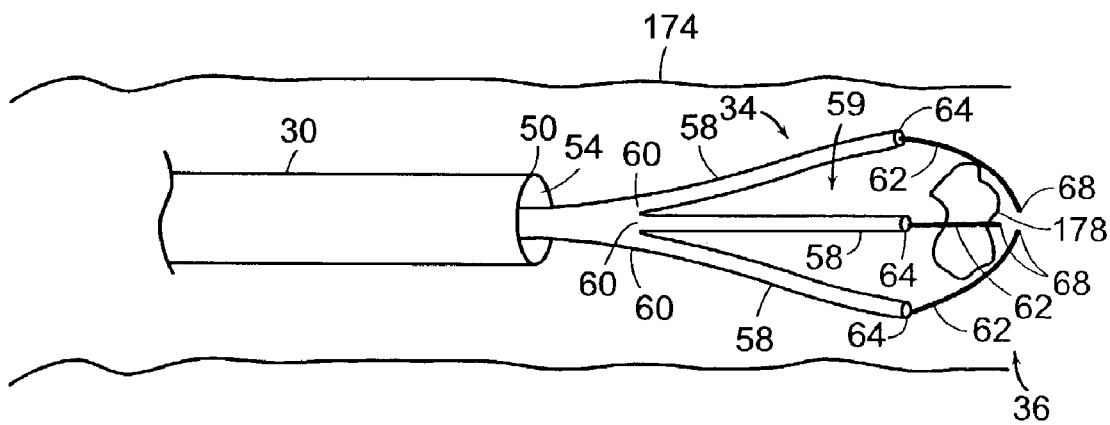
Figure 11D:
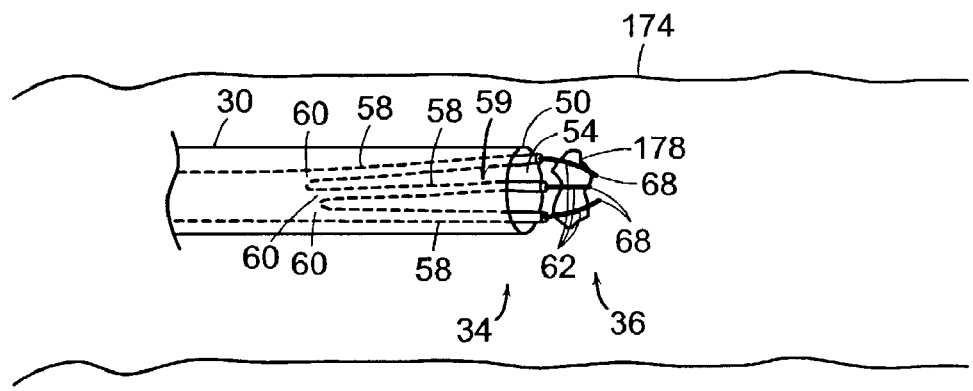
Figure 11E:
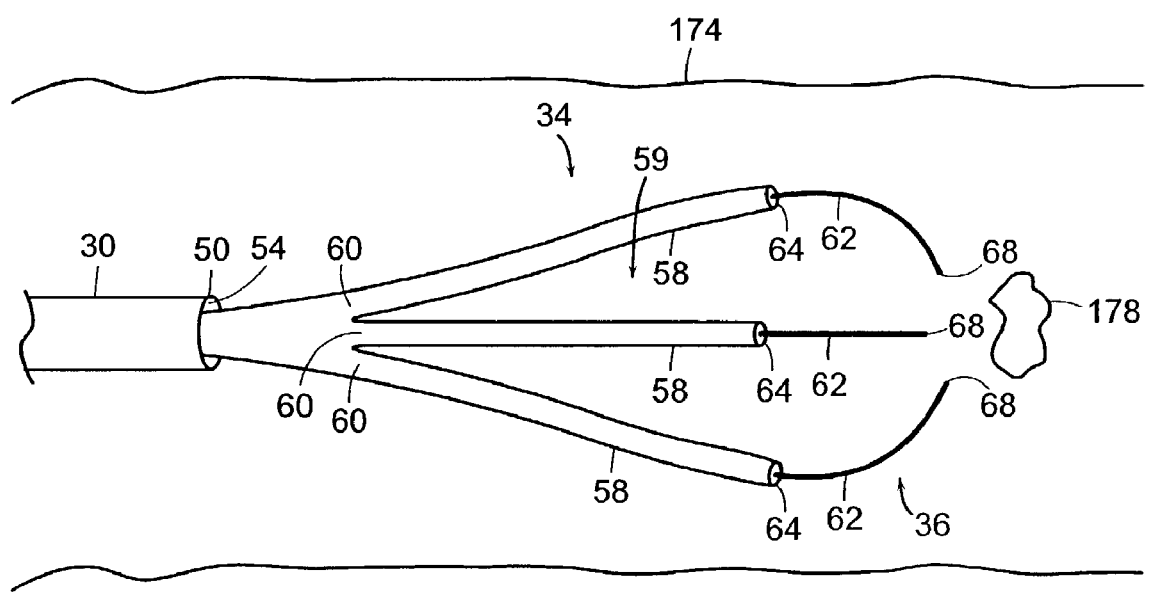

FIGS. 11A-11E illustrate one embodiment of a method for using the surgical retrieval device 22 according to the invention in a clinical setting. Referring to FIG. 11A, according to the invention an operator (e.g., a physician) inserts at least the distal end 36 of the surgical retrieval device 22 into a body tract 174 (e.g., the urethra) of a patient where the material to be retrieved, such as a calculus 178, for example, is located. As shown in FIG. 11A, the surgical retrieval device 22 is inserted into the body tract 174 with the retrieval assembly 34 collapsed within the outer sheath 30. The distal end 50 of the outer sheath 30 of the surgical retrieval device 22 is advanced into the body tract 174 until the distal end 50 of the outer sheath 30 is positioned near the calculus 178. Referring now to FIG. 11B, once the distal end 50 of the outer sheath 30 is positioned close to the calculus 178, the operator extends the legs 58 of the retrieval assembly 34, as discussed above, from the distal end 50 of the outer sheath 30, such that the retrieval assembly 34 achieves the expanded position. Referring now to FIG. 11C, in one embodiment according to the invention, the operator actuates the second thumb slide 74 to extend the prongs 62 beyond the distal ends 64 of the legs 58, as discussed above, to achieve the deployed position. Referring still to FIG. 11C, the prongs 62 are then maneuvered around the calculus 178 until the calculus 178 is entrapped by the prongs 62. By releasing the second thumb slide 74, the return spring 170 is partially returned to its original expanded position and the prongs 62 are partially returned to their original sheathed position within the hollow passageway 66 of each of the legs 58. Both the return spring 170 and the prongs 62 are impeded from fully returning to their original positions by the presence of the calculus 178, which, through the partial expansion of the return spring 170 and the partial retraction of the prongs 62, is now more securely entrapped in the lumen 59 of the retrieval assembly 34 by the prongs 62. As shown in FIG. 11D, in one embodiment according to the invention, the operator may also advance the outer sheath 30 distally to further entrap the calculus 178 within the prongs 62. Once the calculus 178 is securely entrapped within the lumen 59 of the retrieval assembly 34 by prongs 62, the surgical retrieval device 22 and the calculus 178 are removed from the body tract 174 by withdrawing the surgical retrieval device 22 from the body along the same path used to advance the surgical retrieval device 22 into the body. If the operator has difficulty removing the calculus 178 (e.g., the cross-sectional diameter of the expanded retrieval assembly 34 in combination with the calculus 178 is too large to be removed from the body tract 174), the calculus 178 may be released from the prongs 62. To release the calculus 178, the operator withdraws the outer sheath 30 proximally, fully deploys the prongs 62 from the distal ends 64 of the legs 58, and maneuvers the prongs 62 until the calculus 178 is no longer entrapped by the prongs 62, as shown in FIG. 11E. Once the calculus 178 is released, the prongs 62 are withdrawn proximally into the hollow passageways 66 of the protective legs 58 of the retrieval assembly 34 and the protective legs 58 are withdrawn proximally into the lumen 54 of the outer sheath 30, as shown in FIG. 11A. The operator can then safely withdraw the surgical retrieval device 22 from the body tract 174 without causing trauma to the body. Alternatively, to release the calculus 178, the operator simply fully retracts the prongs 62 proximally over the calculus 178 into the hollow passageways 66 of the protective legs 58 of the retrieval assembly 34, fully retracts the protective legs 58 of the retrieval assembly 34 proximally away from the calculus 178 and into the lumen 54 of the outer sheath 30, and safely withdraws the surgical retrieval device 22 from the body tract 174 without causing trauma to the body.

The calculus 178 can be any biological or foreign material. For example, the calculus 178 can be a kidney stone, a ureteral stone, a urethral stone, a urinary bladder stone, a gallbladder stone, or a stone in the biliary tree.

Variations, modifications, and other implementations of what is described herein will occur to those of ordinary skill in the art without departing from the spirit and the scope of the invention. The invention is not to be defined only by the preceding illustrative description.

What is claimed is:

1. A surgical retrieval device, comprising:
   a handle;
   at least one sheath having a proximal end joined to the handle, a distal end, and a lumen;
   a retrieval assembly comprising a plurality of legs, the retrieval assembly achieving a collapsed position when within the lumen of the sheath and an expanded position when beyond the distal end of the sheath, at least one of the legs of the retrieval assembly comprising a hollow passageway for receiving a prong;
   a prong slideably disposed within the hollow passageway such that a distal most end of the prong is withdrawn within the passageway when disposed in a sheathed position; and
   wherein each of the plurality of legs comprises a proximal end fixed to a base of the retrieval assembly and a distal end unfixed to the distal end of any of the other legs.

2. The retrieval device of claim 1 further comprising an actuating mechanism positioned on the handle.

3. The retrieval device of claim 2 wherein the actuating mechanism is coupled to the sheath for reciprocal movement of the sheath to achieve the collapsed position and the expanded position of the retrieval assembly.

4. The retrieval device of claim 2 wherein the actuating mechanism is coupled to the retrieval assembly for reciprocal movement of the retrieval assembly to achieve the collapsed position of the retrieval assembly within the lumen of the sheath and the expanded position of the retrieval assembly beyond the distal end of the sheath.

5. The retrieval device of claim 2 wherein the actuating mechanism comprises a thumb slide.

6. The retrieval device of claim 2 wherein the actuating mechanism comprises a turn knob.

7. The retrieval device of claim 2 wherein the actuating mechanism comprises a lever arm.

8. The retrieval device of claim 1 wherein the retrieval assembly further comprises multiple prongs.

9. The retrieval device of claim 8 wherein at least one prong comprises a modified gripping surface.

10. The retrieval device of claim 8 wherein each leg includes a hollow passageway and a prong is slideably disposed within the hollow passageway of each leg.

11. The retrieval device of claim 10 wherein the prong achieves a sheathed position when located within the hollow passageway of the leg and a deployed position when extended beyond a distal end of the leg.

12. The retrieval device of claim 11 wherein the prong and the leg are oriented differently with respect to the sheath when the prong achieves the deployed position.

13. The retrieval device of claim 1 further comprising an actuating mechanism positioned on the handle.

14. The retrieval device of claim 13 wherein the actuating mechanism is coupled to the prong.

15. The retrieval device of claim 13 wherein the actuating mechanism is coupled to said at least one leg.

16. The retrieval device of claim 1 further comprising a first actuating mechanism, positioned on the handle, for actuating the legs and a second actuating mechanism, positioned on the handle, for actuating the prong.

17. The retrieval device of claim 16, wherein the sheath is secured from movement relative to the handle.

18. The retrieval device of claim 1 wherein a cross-section of the prong is of the same shape as a cross-section of the hollow passageway of the leg.

19. The retrieval device of claim 18 wherein the prong and the hollow passageway have a round cross-section.

20. The retrieval device of claim 18 wherein the prong and the hollow passageway have a rectangular cross-section.

21. The retrieval device of claim 18 wherein the prong and the hollow passageway have a D-shaped cross-section.

22. The retrieval device of claim 18 wherein the prong and the hollow passageway have a V-shaped cross-section.

23. The retrieval device of claim 1 further comprising:
   a first actuating mechanism, positioned on the handle, for moving the sheath relative to the retrieval assembly;
   a second actuating mechanism, positioned on the handle, for moving the prong relative to the retrieval assembly; and
   wherein the retrieval assembly is secured from movement relative to the handle.

24. The retrieval device of claim 1 further comprising:
   a first actuating mechanism, positioned on the handle, for moving the sheath relative to the retrieval assembly;
   a second actuating mechanism, positioned on the handle, for moving the retrieval assembly relative to the prong; and
   wherein the prong is secured from movement relative to the handle.

25. A retrieval assembly for a surgical retrieval device, comprising:

a plurality of legs, each leg comprising a hollow passageway;
a prong disposed within the hollow passageway of each leg; and
wherein the prongs are configured to achieve a sheathed position when located within the hollow passageways of the plurality of legs and a deployed position when extended beyond a distal end of the plurality of legs.

26. The retrieval assembly of claim 25, wherein the retrieval assembly achieves a collapsed position when located within a lumen of a sheath and an expanded position when located beyond a distal end of the sheath, such that when in the expanded position, the legs project outwardly and diverge from one another, and wherein in the deployed position, a tip of each prong points inwardly toward a center of the retrieval assembly.

27. The retrieval assembly of claim 25, wherein the retrieval assembly achieves a collapsed position when located within a lumen of a sheath and an expanded position when located beyond a distal end of the sheath, such that when in the expanded position, a tip of each leg points inwardly toward a center of the retrieval assembly, and wherein in the deployed position, the prongs extend in a straight configuration.

28. The retrieval assembly of claim 25, further comprising a hook positioned at a distal end of each prong.

29. The retrieval assembly of claim 28, wherein each hook is inclined at about 90 degrees relative to a distal end of each prong.

30. The retrieval assembly of claim 25, wherein each of the plurality of legs comprises a proximal end fixed to a base of the retrieval assembly and a distal end unfixed to the distal end of any of the other legs.

31. A method of retrieving a material from a body, comprising the steps of:
inserting a surgical retrieval device into the body, the retrieval device comprising:
a handle;
at least one sheath having a proximal end joined to the handle, a distal end, and a lumen;
a retrieval assembly comprising a plurality of legs, the retrieval assembly achieving a collapsed position when within the lumen of the sheath and an expanded position when beyond the distal end of the sheath, at least one of the legs of the retrieval assembly comprising a hollow passageway for receiving a prong;
a prong slideably disposed within the hollow passageway; and
wherein each of the plurality of legs comprises a proximal end fixed to a base of the retrieval assembly and a distal end unfixed to the distal end of any of the other legs;
positioning the retrieval assembly proximate to the material to be removed with the retrieval assembly in the expanded position;
capturing the material with the retrieval assembly; and
withdrawing the retrieval device from the body to remove the captured material from the body.

32. The method of claim 31 wherein the step of capturing the material comprises capturing a calculus.

33. The method of claim 31, wherein capturing the material with the retrieval assembly further comprises moving the sheath distally relative to the retrieval assembly.

34. The method of claim 31, wherein the retrieval device comprises a prong disposed within the hollow passageway of each leg, and wherein capturing the material with the retrieval assembly further comprises moving at least one prong distally relative to the leg within which the prong is disposed.

35. The method of claim 31, wherein each of the legs of the retrieval assembly comprises a hollow passageway.

36. The method of claim 35, wherein each hollow passageway slideably receives a prong therein.

37. A surgical retrieval device comprising:
a handle;
at least one sheath having a proximal end joined to the handle, a distal end, and a lumen;
a retrieval assembly comprising a plurality of legs, the retrieval assembly achieving a collapsed position when within the lumen of the sheath and an expanded position when beyond the distal end of the sheath, at least one of the legs of the retrieval assembly comprising a hollow passageway and slideably receiving a prong such that a distal most end of the prong is withdrawn within the passageway when disposed in a sheathed position;
wherein a cross-section of the prong is of the same shape as a cross-section of the hollow passageway of the leg; and
wherein the prong and the hollow passageway each have a rounded outer surface and a wedge shaped inner surface.

38. The retrieval device of claim 37, wherein each of the legs of the retrieval assembly comprises a hollow passageway.

39. The retrieval device of claim 38, wherein each hollow passageway slideably receives a prong therein.

40. A surgical retrieval device comprising:
a handle;
at least one sheath having a proximal end joined to the handle, a distal end, and a lumen;
a retrieval assembly comprising a plurality of legs, the retrieval assembly achieving a collapsed position when within the lumen of the sheath and an expanded position when beyond the distal end of the sheath, at least one of the legs of the retrieval assembly comprising a hollow passageway and slideably receiving a prong therein such that a distal most end of the prong is withdrawn within the passageway when disposed in a sheathed position; and
wherein the prong includes an inner surface that is more rough that an outer surface.

41. The retrieval device of claim 40, wherein each of the legs of the retrieval assembly comprises a hollow passageway.

42. The retrieval device of claim 41, wherein each hollow passageway slideably receives a prong therein.

43. A surgical retrieval device, comprising:
a handle;
at least one sheath having a proximal end joined to the handle, a distal end, and a lumen;
a retrieval assembly comprising a plurality of legs, the retrieval assembly achieving a collapsed position when within the lumen of the sheath and an expanded position when beyond the distal end of the sheath, at least one of the legs of the retrieval assembly comprising a hollow passageway;
a prong disposed within the passageway of the at least one leg;
a first actuating mechanism, positioned on the handle, for actuating the legs;
a second actuating mechanism, positioned on the handle, for actuating the prong; and wherein each of the plurality of legs comprises a proximal end fixed to a base of the retrieval assembly and a distal end unfixed to the distal end of any of the other legs.

44. The retrieval device of claim 43, wherein the sheath is secured from movement relative to the handle.

45. The retrieval device of claim 43, wherein the retrieval assembly is secured from movement relative to the handle.

46. The retrieval device of claim 43, wherein the prong is secured from movement relative to the handle.

47. The retrieval device of claim 43, wherein each of the legs of the retrieval assembly comprise a hollow passageway and slideably receive a prong therein.

48. The retrieval device of claim 47, wherein in the expanded position, the legs project outwardly and diverge from one another, and wherein in the deployed position, a tip of each prong points inwardly toward a center of the retrieval assembly.

49. The retrieval device of claim 43, wherein in the expanded position, a tip of each leg points inwardly toward a center of the retrieval assembly, and wherein in the deployed position, the prongs extend in a straight configuration.

* * * * *